United States Patent
Suzuki et al.

(10) Patent No.: US 9,266,790 B2
(45) Date of Patent: Feb. 23, 2016

(54) METHOD FOR PRODUCING OLEFIN

(75) Inventors: Nobuyoshi Suzuki, Wakayama (JP); Hideo Tahara, Hannan (JP); Daisuke Ishihara, Wakayama (JP); Hiroshi Danjo, Wakayama (JP); Ilhyong Ryu, Suita (JP); Takahide Fukuyama, Sakai (JP)

(73) Assignee: Kao Corporation, Tokyo (JP)

( * ) Notice: Subject to any disclaimer, the term of this patent is extended or adjusted under 35 U.S.C. 154(b) by 429 days.

(21) Appl. No.: 13/976,706

(22) PCT Filed: Aug. 4, 2011

(86) PCT No.: PCT/JP2011/067825
§ 371 (c)(1),
(2), (4) Date: Jun. 27, 2013

(87) PCT Pub. No.: WO2012/090544
PCT Pub. Date: Jul. 5, 2012

(65) Prior Publication Data
US 2013/0296626 A1 Nov. 7, 2013

(30) Foreign Application Priority Data
Dec. 28, 2010 (JP) .................. 2010-291848

(51) Int. Cl.
*C07C 1/20* (2006.01)
*C07C 1/207* (2006.01)

(52) U.S. Cl.
CPC ........... *C07C 1/2078* (2013.01); *C07C 2523/04* (2013.01); *C07C 2531/20* (2013.01); *C07C 2531/24* (2013.01); *C07C 2531/30* (2013.01)

(58) Field of Classification Search
USPC .................. 585/638, 639, 640, 641
See application file for complete search history.

(56) References Cited

U.S. PATENT DOCUMENTS

| 3,530,198 A * | 9/1970 | Fenton ............... C07C 1/00 568/835 |
| 5,077,447 A | 12/1991 | Miller et al. |
| 2011/0190564 A1 | 8/2011 | Suzuki et al. |
| 2012/0226085 A1 | 9/2012 | Ishihara et al. |

FOREIGN PATENT DOCUMENTS

| EP | 2 325 156 A1 | 5/2011 |
| JP | 2010-168340 | 8/2010 |
| JP | 2011-168528 | 9/2011 |
| WO | WO 2010/024420 A1 | 3/2010 |
| WO | WO 2011/058990 A1 | 5/2011 |

OTHER PUBLICATIONS

Chepaikin et al. Physical Chemistry vol. 437 (2010) p. 41-44.*
Extended European Search Report issued Jun. 20, 2014 in Patent Application No. 11852269.7.
International Preliminary Report on Patentability and Written Opinion issued Jul. 2, 2013 in Application No. PCT/JP2011/067825.
L. J. Goossen, et al., "A mild and efficient protocol for the conversion of carboxylic acids to olefins by a catalytic decarbonylative elimination reaction", Chemical Communications, No. 6, 2004, pp. 724-725.
Takahide O. Maetani, et al., "Iron-catalyzed decarbonylation of aliphatic carboxylic acids", Chemical Society of Japan, vol. 90, No. 4, Mar. 12, 2010, p. 1202 and Cover Page (with English Abstract).
Takahide O. Maetani, et al., "Iridium-catalyzed decarbonylation of aliphatic carboxylic acids leading to internal alkenes", Chemical Society of Japan, vol. 89, No. 2, 2009, p. 990 and Cover Page (with English Abstract).

* cited by examiner

*Primary Examiner* — In Suk Bullock
*Assistant Examiner* — Sharon Pregler
(74) *Attorney, Agent, or Firm* — Oblon, McClelland, Maier & Neustadt, L.L.P.

(57) ABSTRACT

The present invention discloses a method for producing an olefin through decarbonylation of a carboxylic acid having a β-hydrogen atom or a derivative thereof in the presence of a catalyst containing at least one metal element selected from Groups 9, 10, and 11 metals under conditions with a concentration of carbon monoxide of not less than 41 mmol/L.

9 Claims, No Drawings

US 9,266,790 B2

METHOD FOR PRODUCING OLEFIN

FIELD OF THE INVENTION

The present invention relates to a method for producing an olefin from a carboxylic acid having a β-hydrogen atom or a derivative thereof, and more particularly to a method for producing an olefin suitably used as an intermediate for manufacturing surfactants, various chemicals, and pharmaceuticals.

BACKGROUND OF THE INVENTION

To producing an olefin having a desired chain length, commonly known is a method of oligomerizing a short-chain olefin such as ethylene to synthesize an α olefin. The method of oligomerization unfortunately fails to produce only an olefin having a desired chain length at high yield due to distribution in the degree of polymerization.

There are also known methods for producing an olefin from a carboxylic acid, including a method of production from a carboxylic acid in the presence of a Pd complex catalyst (U.S. Pat. No. 3,530,198), a method of production of an α olefin from a carboxylic acid in the presence of an acid anhydride and a catalyst containing an element selected from Group 8, Group 9, and Group 10 metals and copper (U.S. Pat. No. 5,077,447), and a method of production of an α olefin from a carboxylic acid in the presence of a Pd complex catalyst and a pivalic anhydride (Chem. Commun., 724, (2004)). These methods have employed a special additive or a particularly high reaction temperature of not less than 250° C. to enhance olefin production efficiency, but unfortunately resulting in an unsatisfactory yield of a desired olefin.

Recently, the present inventors have found that use of a catalyst containing an iodine element and at least one metal element selected from Groups 6 to 11, or a combination of an iodide and a catalyst containing a metal element selected from Group 8, Group 9, and Group 10 and copper could produce an olefin at high yield under relatively mild conditions, and disclosed in JP-A2010-168340, which corresponds to WO-A2010/024420.

SUMMARY OF THE INVENTION

The present invention provides a method for producing an olefin, including conducting decarbonylation of a carboxylic acid having a β-hydrogen atom or a derivative thereof in the presence of a catalyst comprising at least one metal element selected from Group 9 metals, Group 10 metals and Group 11 metals under conditions with a concentration of carbon monoxide of not less than 41 mmol/L in the gas phase during the reaction.

DETAILED DESCRIPTION OF THE INVENTION

The present invention provides the method for producing an olefin, that method can produce a desired olefin at high yield.

For producing an olefin from a carboxylic acid through decarbonylation, considering equilibrium of the decarbonylation, a decreased concentration of carbon monoxide in a reaction system is thought to be advantageous to increase an olefin yield, and carbon monoxide generating from the reaction has been tried to be removed from the system. In contrast to this knowledge, the present inventors have unexpectedly found that a catalyst containing a specific metal element can provide an increased olefin yield even under conditions with a relatively high concentration of carbon monoxide, and accomplished the present invention.

According to the method of the present invention, an olefin suitably used as an intermediate for manufacturing surfactants and various chemicals can be synthesized at high yield from a carboxylic acid or a derivative thereof.

The present invention can use any carboxylic acid having a β-hydrogen atom or a derivative thereof, provided that the carboxylic acid or a derivative thereof has at least one hydrogen atom at β-position of the carbonyl group. The carboxylic acid or a derivative thereof may be saturated or unsaturated, be partially cyclized, contain a heteroatom, or contain plural carbonyl groups. The present invention preferably uses a saturated monocarboxylic acid or a derivative thereof. Examples of the derivative of the carboxylic acid having a β-hydrogen atom include anhydrides, halides, esters, and amides of the carboxylic acid. Among these derivatives, preferred are anhydrides and halides of the carboxylic acid, and more preferred are anhydrides of the carboxylic acid.

Specific examples of the carboxylic acid having a β-hydrogen atom include 3-methylbutanoic acid, caproic acid, caprylic acid, capric acid, lauric acid, myristic acid, palmitic acid, stearic acid, eicosanoic acid, behenic acid, 9-decenoic acid, 10-undecenoic acid, oleic acid, 2,4-hexadienoic acid, 6-octadecynoic acid, ricinoleic acid, adipic acid, azelaic acid, 3-phenylpropionic acid, hydnocarpic acid, and gorlic acid.

Specific examples of the anhydride of the carboxylic acid having a β-hydrogen atom include 3-methylbutanoic anhydride, caproic anhydride, caprylic anhydride, capric anhydride, lauric anhydride, myristic anhydride, palmitic anhydride, stearic anhydride, eicosanoic anhydride, behenic anhydride, 9-decenoic anhydride, 10-undecenoic anhydride, oleic anhydride, 2,4-hexadienoic anhydride, 6-octadecynoic anhydride, ricinoleic anhydride, succinic anhydride, adipic anhydride, azelaic anhydride, 3-phenylpropionic anhydride, hydnocarpic anhydride, and gorlic anhydride. The anhydride may be a carboxylic anhydride obtained by condensating the above exemplified carboxylic acid having a β-hydrogen atom with formic acid, acetic acid, propionic acid or butyric acid or condensating the above exemplified carboxylic acid with another above exemplified carboxylic acid. Moreover, an anhydride having a β-hydrogen atom may be produced by mixing an acid anhydride having a low boiling point, such as acetic anhydride and pivalic anhydride, with the above exemplified carboxylic acid having a β-hydrogen atom, in advance.

Examples of the halide of the carboxylic acid having a β-hydrogen atom include a chloride, a bromide or an iodide of 3-methylbutanoic acid, caproic acid, caprylic acid, capric acid, lauric acid, myristic acid, palmitic acid, stearic acid, eicosanoic acid, behenic acid, 9-decenoic acid, 10-undecenoic acid, oleic acid, 2,4-hexadienoic acid, 6-octadecynoic acid, ricinoleic acid, adipic acid, azelaic acid, 3-phenylpropionic acid, hydnocarpic acid, gorlic acid or the like.

Specific examples of the ester of the carboxylic acid having a β-hydrogen atom include a methyl ester, an ethyl ester or the like of 3-methylbutanoic acid, caproic acid, caprylic acid, capric acid, lauric acid, myristic acid, palmitic acid, stearic acid, eicosanoic acid, behenic acid, 9-decenoic acid, 10-undecenoic acid, oleic acid, 2,4-hexadienoic acid, 6-octadecynoic acid, ricinoleic acid, adipic acid, azelaic acid, 3-phenylpropionic acid, hydnocarpic acid, gorlic acid or the like.

Specific examples of the amide of the carboxylic acid having a β-hydrogen atom include an amide, a monomethylamide, a dimethylamide, a diethylamide or the like of 3-methylbutanoic acid, caproic acid, caprylic acid, capric acid, lauric acid, myristic acid, palmitic acid, stearic acid, eicosanoic acid, behenic acid, 9-decenoic acid, 10-undecenoic acid, oleic acid, 2,4-hexadienoic acid, 6-octadecynoic acid, ricinoleic acid, adipic acid, azelaic acid, 3-phenylpropionic acid, hydnocarpic acid, gorlic acid or the like.

The carboxylic acid having a β-hydrogen atom or a derivative thereof has preferably a carboxylic acid or a carboxylic group (at least one carboxylic group for the carboxylic anhydride) with 3 to 22-carbon atoms, more preferably 8 to 18, and even more preferably 12 to 18. In use of an unsaturated carboxylic acid or a derivative thereof as a starting material, a produced olefin will have one more double bond than the starting material.

In the method of the present invention, the carboxylic acid having a β-hydrogen atom or a derivative thereof is subjected to decarbonylation in the presence of a catalyst containing at least one metal element selected from Groups 9, 10, and 11 metals, including Co, Rh, Ir, Ni, Pd, Pt, Cu, Ag, and Au, and the like.

The decarbonylation is preferably conducted in the presence of an iodide and a catalyst containing at least one metal element selected from Groups 9, 10, and 11 metals (hereinafter, referred to as Aspect 1) or in the presence of a catalyst containing an iodine element and at least one metal element selected from Groups 9, 10, and 11 metals (hereinafter, referred to as Aspect 2), or may be conducted in the presence of the catalyst as in Aspect 1 but without the iodide (hereinafter, referred to as Aspect 3).

(Aspect 1)

Aspect 1 uses a catalyst containing at least one metal element selected from Groups 9, 10, and 11 metals. From the viewpoints of reactivity and selectivity, the at least one metal element is preferably selected from Co, Rh, Ir, Ni, Pd, Pt, and Cu, more preferably Co, Rh, Ir, Ni, Pd, and Cu, and even more preferably Ni. Specific examples of the catalyst containing at least one metal element selected from Groups 9, 10, and 11 metals include $[RhCl(CO)_2]_2$, $(Ph_3P)_2Rh(CO)Cl$, $RhCl_3$, $(Ph_3P)_2NiCl_2$, $NiCl_2$, $(Ph_3P)_2PdCl_2$, $PdCl_2$, $(Ph_3P)_2CoCl_2$, $CoCl_2$, $(Ph_3P)_2PtCl_2$, $PtCl_2$, $(Ph_3P)_2Ir(CO)Cl$, $Ir(CO)_3Cl$, $IrCl_3$, $(Ph_3P)_3CuCl$, and $CuCl$, in which Ph represents a phenyl group (the same applies below). Among these catalysts, preferred are $[RhCl(CO)_2]_2$ $(Ph_3P)_2PdCl_2$, $(Ph_3P)_2CoCl_2$, $Ir(CO)_3Cl$, $(Ph_3P)_2NiCl_2$, CuCl, and the like, and particularly preferred is $(Ph_3P)_2NiCl_2$.

In Aspect 1, the catalyst is preferably used in an amount corresponding to 0.00001 to 0.8 mol, more preferably 0.0001 to 0.5 mol, even more preferably 0.001 to 0.4 mol, and even more preferably 0.005 to 0.3 mol per a metal atom to 1 mol of the carboxylic acid having a β-hydrogen atom or a derivative thereof.

Aspect 1 can use an iodide without any limitation. Examples of the iodide include iodides of elements belonging to Groups 1 to 8 and 12 to 14 and quaternary ammonium compounds represented by the formula (1):

$$[R-(Y)_n]_4N^+I^- \quad (1)$$

wherein, R represents a hydrocarbon group having 1 to 22 carbon atoms; Y represents a group —Z—$(CH_2)_m$—, wherein Z represents an ether group, an amino group, an amide group or an ester group, or more specifically —O—, —NH—, —CONH—, —NHCO—, —COO— or —OCO—, and m represents a number of from 1 to 6, and n represents 0 or 1; and plural R's, plural Y's, and plural n's each are the same as or different from one another, and a cyclic structure may be formed between $[R-(Y)_n]$'s.

An iodide of an element selected from elements of Groups 1 to 8 and elements of Groups 12 to 14 can be used without limitation. Preferably used are iodides of elements belonging to Groups 1 and 12. Specific examples of the iodide include KI, LiI, NaI, and $ZnI_2$. Preferred are KI and NaI.

The quaternary ammonium compound preferably has the formula (1) in which R represents an alkyl group having 1 to 7 carbon atoms or a benzyl group, and more preferably an alkyl group having 1 to 7 carbon atoms, and n represents 0. The quaternary ammonium compound is more preferably $Et_4N^+I^-$ or $(n-Butyl)_4N^+I^-$ (in which, Et represents an ethyl group, and n-Butyl represents an n-butyl group), and more particularly preferably $Et_4N^+I^-$.

In Aspect 1, the iodide is preferably used in an amount of 0.001 to 10 mol, more preferably 0.01 to 3 mol, to 1 mol of carboxylic acid having a β-hydrogen atom or derivative thereof.

In Aspect 1, the catalyst containing at least one metal element selected from Groups 9, 10, and 11 metals may be used together with a ligand containing a Group 15 element. Examples of the ligand include N-heterocyclic carbene ligands, pyridine ligands such as 2,2-bipyridyl and pyridine, arsenic ligands, nitrile ligands such as acetonitrile and benzonitrile, isonitrile ligands, and organophosphorous ligands. Organophosphorous ligands are more preferred. Specific examples of the organophosphorous ligand include dimethylphenylphosphine, diethylphenylphosphine, methyldiphenylphosphine, ethyldiphenylphosphine, cyclohexyldiphenylphosphine, tricyclohexylphosphine, triisopropylphosphine, tributylphosphine, tri-t-butylphosphine, tribenzylphosphine, triphenylphosphine, tris(p-methoxyphenyl)phosphine, and 1,2-bis(diphenylphosphino)ethane. Among these ligands, preferred are triphenylphosphine, dimethylphenylphosphine, diethylphenylphosphine, methyldiphenylphosphine, ethyldiphenylphosphine, and 1,2-bis(diphenylphosphino)ethane, more preferred are triphenylphosphine and 1,2-bis(diphenylphosphino)ethane, and particularly preferred is triphenylphosphine. These ligands may be used alone or in combination of two or more of them.

For a good stability of the catalyst and a good reaction rate, the ligand containing a Group 15 element is preferably used in an amount of 0.3 to 100 mol, including that originally coordinated to the catalyst, to 1 mol of the metal atom of the catalyst, more preferably 0.5 to 20 mol, and even more preferably 2 to 10 mol.

In Aspect 1 of the present invention, the decarbonylation can be conducted at a concentration of carbon monoxide without limitation in the gas phase during the reaction, provided that it is not less than 41 mmol/L. For a good stability of the catalyst and a good reaction rate, the concentration is preferably 60 mmol/L to 2400 mmol/L, and more preferably 80 mmol/L to 1000 mmol/L.

A concentration of carbon monoxide in a gas phase can be determined and controlled by a simple measurement of a pressure of a reaction system. 41 mmol/L refers to the number of moles of perfect gas per unit volume at normal temperature at normal pressure (25° C., 101 kPa), correspondingly when the gas phase of the reaction system has been substituted with carbon monoxide at 25° C. under normal pressure. The reaction system sealed in this state varies a pressure but not the number of molecules when elevated to a predetermined reaction temperature (e.g., 250° C.), and accordingly undergoes the reaction at an unchanged concentration of carbon monoxide in the gas phase, 41 mmol/L. In the same way, in cases of filling a gas phase with carbon monoxide under a predetermined pressure (e.g., 608 kPa, corresponding to about 246 mmol/L) at a room temperature, a reaction system sealed in this state undergoes the reaction at a predetermined concentration (246 mmol/L) by elevating to a predetermined temperature. It is noted that a concentration of carbon monoxide in a gas phase may decrease due to dissolution of carbon monoxide in a liquid phase, while an increase of carbon monoxide, generated in the reaction, takes place. A fine adjustment is accordingly necessary.

An alternative method for controlling a concentration of carbon monoxide includes flowing carbon monoxide into a reaction system under a predetermined pressure at a predetermined temperature. For example, a concentration of carbon monoxide in a gas phase can be kept to 246 mmol/L by flowing carbon monoxide under a pressure of 1067 kPa (608× (273.15+250)/(273.15+25)) at 250° C. It is noted that, at high temperature, the reaction system gets vapor pressure from coexistent components such as water generating from the reaction, a reactant fatty acid (derivative), a produced olefin, and an optional solvent, while partially reducing pressure on the upper part of a reactor and in a pipe. Therefore, in order to precisely control a pressure, a blank test should be preliminarily performed to determine a contributing rate of a partial pressure of each component and correct the pressure.

In this method, water and an intended product generating from the reaction can be distilled off from the reaction system, while continuing the reaction.

A concentration of carbon monoxide in a gas phase can be precisely estimated by taking a sample from the gas phase. For example, a part of a gas phase can be sent into a looped pipe having a known volume, set at the same temperature as the inner temperature of the reactor to be collected as a sample gas, and the taken-out sample gas can be analyzed by a known method for determining carbon monoxide. Examples of the method for determining carbon monoxide include gas chromatography with a methanizer, measurement with a potential-controlled amperometric sensor, with an infrared sensor, or with a Kitagawa gas detector tube system, and a method including having the sample absorbed in an aqueous solution containing a metal ion such as Ni and quantifying it with titration or absorption spectrometry.

In the method for producing an olefin of the present invention, the gas phase may contain other gas in addition to carbon monoxide. For preventing adverse effects such as deceleration of the reaction and catalyst poisoning, the other gas introduced into the gas phase is preferably an inert gas, for example, nitrogen, carbon dioxide, argon, and helium. Nitrogen and argon are particularly preferred.

The method for producing an olefin of the present invention is characterized by being performed under reaction conditions with a high concentration of carbon monoxide, or in a carbon monoxide-rich environment though the method is based on elimination reaction of carbon monoxide.

In Aspect 1 of the present invention, for achieving good olefin selectivity, a temperature in the decarbonylation is preferably 20 to 300° C., more preferably 80 to 270° C., and even more preferably 120 to 260° C.

In Aspect 1 of the present invention, the reaction undergoes without an acid anhydride having no β-hydrogen atom, but may undergo with an acid anhydride having no β-hydrogen atom. In this case, an amount of the acid anhydride having no β-hydrogen atom used is preferably not more than 10 mol, and more preferably not more than 2 mol to 1 mol of the carboxylic acid having a β-hydrogen atom or a derivative thereof. The amount is also preferably not less than 0.01 mol. The acid anhydride having no β-hydrogen atom preferred for use is acetic anhydride.

Aspect 3 of the present invention can be performed in the same way as in Aspect 1, except that the iodide is not used.

(Aspect 2)

Aspect 2 of the present invention uses a catalyst that is a compound containing an iodine element and at least one metal element selected from Groups 9, 10, and 11 metals. From the viewpoints of reactivity and selectivity, the at least one metal element selected from Groups 9, 10, and 11 metals is preferably selected from Co, Rh, Ir, Ni, Pd, Pt, Cu, Ag, and Au, more preferably Co, Rh, Ir, Ni, and Pt, and even more preferably Ni. Specific examples of the catalyst containing an iodine element and at least one metal element selected from Groups 9, 10, and 11 metals include $CoI_2$, $CoI_2(CO)(C_5H_5)$, $CoI_2(PPh_3)(C_5H_5)$, $CoI_2(PPh_3)_2$, $RhI_3$, $[RhI(CO)_2]_2$, $RhI(PPh_3)_3$, $IrI_4$, $IrI(CO)(PPh_3)_2$, $NiI_2$, $NiI_2(NH_3)_6$, $NiI(1,5$-cyclooctadiene$)$, $NiI(PPh_3)_3$, $PdI_2$, $PdI_2(PPh_3)_2$, $PdI(CH_3)(PPh_3)_2$, $PtI_2$, $[Pt_2I_2(H_2NCH_2CH_2NH_2)_2](NO_3)_2$, $PtI_2(1,5$-cyclooctadiene$)$, $PtI(CH_3)_3$, $PtI(CH_3)(PEt_3)_2$, $CuI$, $AgI$, $AuI$, and $AuI(CH_3)_2(PPh_3)$, in which Ph represents a phenyl group, and Et represents an ethyl group (the same applies below). Among these catalysts, preferred are $CoI_2$, $RhI_3$, $[RhI(CO)_2]_2$, $IrI(CO)(PPh_3)_2$, $NiI_2$, and $PtI_2$, and more preferred is $NiI_2$.

In Aspect 2, the catalyst is preferably used in an amount corresponding to 0.00001 to 0.8 mol, more preferably 0.0001 to 0.5 mol, even more preferably 0.001 to 0.4 mol, and still even more preferably 0.005 to 0.3 mol per a metal atom to 1 mol of carboxylic acid having a β-hydrogen atom or derivative thereof.

In Aspect 2, the compound containing an iodine element and at least one metal element selected from Groups 9, 10, and 11 metals may be used together with a ligand containing a Group 15 element. Examples of the ligand include N-heterocyclic carbene ligands, pyridine ligands such as 2,2-bipyridyl and pyridine, arsenic ligands, nitrile ligands such as acetonitrile and benzonitrile, isonitrile ligands, and organophosphorous ligands. Organophosphorous ligands are more preferred. Specific examples of the organophosphorous ligand include dimethylphenylphosphine, diethylphenylphosphine, methyldiphenylphosphine, ethyldiphenylphosphine, cyclohexyldiphenylphosphine, tricyclohexylphosphine, triisopropylphosphine, tributylphosphine, tri-t-butylphosphine, tribenzylphosphine, triphenylphosphine, tris (p-methoxyphenyl)phosphine, and 1,2-bis (diphenylphosphino)ethane. Among these ligands, preferred are triphenylphosphine, dimethylphenylphosphine, diethylphenylphosphine, methyldiphenylphosphine, ethyldiphenylphosphine, and 1,2-bis(diphenylphosphino) ethane, more preferred are triphenylphosphine and 1,2-bis(diphenylphosphino)ethane, and particularly preferred is triphenylphosphine. These ligands may be used alone or in combination of two or more of them.

From the viewpoints of olefin productivity and operability, the ligand containing a Group 15 element is preferably used in an amount of less than 100 mol including that originally coordinated to the catalyst to 1 mol of metal atom of the catalyst, more preferably less than 12 mol, and even ore preferably less than 4 mol.

In Aspect 2 of the present invention, the decarbonylation can be conducted at a concentration of carbon monoxide in the gas phase of the reaction, provided that it is not less than 41 mmol/L, in the same way as in Aspect 1. For good stability of a catalyst and good reaction rate, the concentration is preferably 60 mmol/L to 2400 mmol/L, and more preferably 80 mmol/L to 1000 mmol/L.

In Aspect 2 of the present invention, a concentration of carbon monoxide in a gas phase can be determined and controlled by the same method as in Aspect 1. Preferably employed are methods of introducing carbon monoxide in a reactor at a predetermined pressure at normal temperature, sealing the reactor, and elevating a temperature to react, and of reacting with a carbon monoxide flow under a predetermined pressure at a predetermined temperature.

The method for producing an olefin of the present invention is characterized by being performed under reaction conditions with a high concentration of carbon monoxide, or in a carbon monoxide-rich environment though the method is based on elimination reaction of carbon monoxide.

In Aspect 2 of the present invention, for achieving good olefin selectivity, a temperature in the decarbonylation is preferably 20 to 300° C., more preferably 80 to 270° C., and even more preferably 120 to 260° C.

In Aspect 2 of the present invention, the reaction undergoes without adding an acid anhydride having no β-hydrogen atom, but may undergo with an acid anhydride having no β-hydrogen atom. In this case, an amount of the acid anhydride having no β-hydrogen atom used is preferably not more than 10 mol, and more preferably not more than 2 mol to 1 mol of the carboxylic acid having a β-hydrogen atom or a derivative thereof. The amount is also preferably not less than 0.01 mol. The acid anhydride having no β-hydrogen atom preferred for use is acetic anhydride.

The method of the present invention can produce not only an olefin having a terminal double bond, but also an internal olefin having a double bond inside, isomerized from the terminal olefin.

EXAMPLES

The following Examples demonstrate the present invention. Examples are intended to illustrate the present invention and not to limit the present invention.

Hereinafter, unless otherwise stated, "%" refers to "% by mole". Examples relating to Aspect 1 are assigned with "Example 1-n". Examples relating to Aspects 2 and 3 are assigned with "Example 2-n" and "Example 3-n", respectively.

Example 1-1

In a 30 mL stain-less auto clave containing a stirring bar, 284.5 mg (1.0 mmol) of stearic acid, 6.5 mg (0.01 mmol) of $NiCl_2(PPh_3)_2$, 5.2 mg (0.02 mmol) of triphenylphosphine ($PPh_3$) and 16.6 mg (0.1 mmol) of potassium iodide were placed. The inner atmosphere was replaced with carbon monoxide three times by introducing carbon monoxide under 3000 kPa (absolute pressure) at a room temperature (25° C.) and reducing the pressure to the normal pressure. Then, carbon monoxide was introduced under 608 kPa (absolute pressure) at a room temperature. The reaction system was sealed, started with being stirred and then heated, the stirring being continued at 250° C. for 3 hours. In the reaction system, a gas phase contained carbon monoxide at a concentration of 246 mmol/L. After the end of heating, the reaction mixture was allowed to cool to a room temperature (25° C.). Low-boiling matters were distilled off under reduced pressure and then anisole was added as an internal standard. The mixture was analyzed by $^1$H-NMR spectroscopy to quantify products by comparing integrals of signals of α-protons of stearic acid, vinyl protons of a terminal olefin, vinyl protons of an internal olefin, and protons of the methyl group of anisole standard.

A yield of olefins was 31% (terminal olefin:internal olefin(s) (molar ratio)=42:58) of the starting stearic acid.

Examples 1-2 to 1-5

These Examples were conducted in the same way as in Example 1-1, except that the kinds of the catalysts, the amounts of the catalysts and the amount of triphenylphosphine were changed as shown in Table 1.

Comparative Examples 1-1 to 1-5

These Examples were conducted in the same way as in Example 1-1, except that the kinds of the catalysts, the amounts of the catalysts and the amount of triphenylphosphine were changed as shown in Table 1, the reactor was a 20 mL recovery flask that was subjected to atmosphere substitution with nitrogen three times by depressurizing and releasing with nitrogen and connected to a vacuum pump, and the reaction was conducted under 33 kPa (absolute pressure). In the reaction system, a gas phase contained carbon monoxide at a concentration from 0 mmol/L (initial stage of the reaction) to 3.8 mmol/L (maximum value at the end of the reaction).

The maximum value at the end of the reaction is a value estimated as follows:

when the reaction generates 0.1 mol of CO, also generating 0.1 mol of water; at such a high temperature as 250° C. under vacuum, supposing that water totally vaporizes, it is accordingly considered that a half of 33 kPa is CO; therefore, a maximum concentration of carbon monoxide in a gas phase is 33/2/101.3÷22.4×273.15/(273.15+250)×1000=3.8 mmol/L.

Results of Examples 1-1 to 1-5 and Comparative Examples 1-1 to 1-5 are collectively shown in Table 1.

TABLE 1

|  |  | Example | | | | |
|---|---|---|---|---|---|---|
|  |  | 1-1 | 1-2 | 1-3 | 1-4 | 1-5 |
| Catalyst | Kind | $NiCl_2(PPh_3)_2$ | $[RhCl(CO)_2]_2$ | $IrCl(CO)_3$ | $PdCl_2(PPh_3)_2$ | CuCl |
|  | Amount (%)*1 | 1 | 0.5 | 1 | 1 | 1 |
| Iodide | Kind | KI | KI | KI | KI | KI |
|  | Amount (%)*1 | 10 | 10 | 10 | 10 | 10 |
| Ligend | Kind | $PPh_3$ | — | — | $PPh_3$ | $PPh_3$ |
|  | Amount (%)*1*2 | 2 | — | — | 2 | 4 |
| Reaction temperature (° C.) |  | 250 | 250 | 250 | 250 | 250 |
| Pressure (kPa, absolute pressure) |  | 608 (when introduced) | 608 (when introduced) | 608 (when introduced) | 608 (when introduced) | 608 (when introduced) |
| CO concentration in gas phase (mmol/L) |  | 246 | 246 | 246 | 246 | 246 |
| Yield of olefin (%) |  | 31 | 8 | 8 | 16 | 6 |

TABLE 1-continued

| | | | | | | |
|---|---|---|---|---|---|---|
| ratio of terminal olefin and internal olefin (%) | Terminal olefin | 42 | 53 | >99 | <1 | >99 |
| | Internal olefin | 58 | 47 | <1 | >99 | <1 |

| | | Comparative example | | | | |
|---|---|---|---|---|---|---|
| | | 1-1 | 1-2 | 1-3 | 1-4 | 1-5 |
| Catalyst | Kind | $NiCl_2(PPh_3)_2$ | $[RhCl(CO)_2]_2$ | $IrCl(CO)_3$ | $PdCl_2(PPh_3)_2$ | CuCl |
| | Amount (%)*[1] | 1 | 0.5 | 1 | 1 | 1 |
| Iodide | Kind | KI | KI | KI | KI | KI |
| | Amount (%)*[1] | 10 | 10 | 10 | 10 | 10 |
| Ligend | Kind | $PPh_3$ | — | — | $PPh_3$ | $PPh_3$ |
| | Amount (%)*[1]*[2] | 2 | — | — | 2 | 4 |
| Reaction temperature (° C.) | | 250 | 250 | 250 | 250 | 250 |
| Pressure (kPa, absolute pressure) | | 33 | 33 | 33 | 33 | 33 |
| CO concentration in gas phase (mmol/L) | | 0~3.8 | 0~3.8 | 0~3.8 | 0~3.8 | 0~3.8 |
| Yield of olefin (%) | | 13 | 0 | 3 | 13 | 0 |
| ratio of terminal olefin and internal olefin (%) | Terminal olefin | 12 | — | 0 | 10 | — |
| | Internal olefin | 88 | — | 100 | 90 | — |

*[1]A percentage by mole to a fatty acid
*[2]Excluding a ligand originally coordinated to a catalyst Examples 1-6 to 1-8

These Examples were conducted in the same way as in Example 1-1, except that respective reaction pressures as shown in Table 2 were used.

Results of Examples 1-1 and 1-6 to 1-8 and Comparative Example 1-1 are collectively shown in Table 2.

TABLE 2

| | | Example | | | | Comparative example |
|---|---|---|---|---|---|---|
| | | 1-1 | 1-6 | 1-7 | 1-8 | 1-1 |
| Catalyst | Kind | $NiCl_2(PPh_3)_2$ | $NiCl_2(PPh_3)_2$ | $NiCl_2(PPh_3)_2$ | $NiCl_2(PPh_3)_2$ | $NiCl_2(PPh_3)_2$ |
| | Amount (%)*[1] | 1 | 1 | 1 | 1 | 1 |
| Iodide | Kind | KI | KI | KI | KI | KI |
| | Amount (%)*[1] | 10 | 10 | 10 | 10 | 10 |
| Amount of ligand $PPh_3$ (%)*[1]*[2] | | 2 | 2 | 2 | 2 | 2 |
| Reaction temperature (° C.) | | 250 | 250 | 250 | 250 | 250 |
| Pressure (kPa, absolute pressure) | | 608 (when introduced) | 203 (when introduced) | 304 (when introduced) | 1114 (when introduced) | 33 |
| CO concentration in gas phase (mmol/L) | | 246 | 82 | 123 | 462 | 0~3.8 |
| Yield of olefin (%) | | 31 | 17 | 20 | 14 | 13 |
| ratio of terminal olefin and internal olefin (%) | Terminal olefin | 42 | 23 | 55 | 70 | 12 |
| | Internal olefin | 58 | 77 | 45 | 30 | 88 |

*[1]A percentage by mole to a fatty acid
*[2]Excluding a ligand originally coordinated to a catalyst Example 1-9

This Example was conducted in the same way as in Example 1-1, except that stearic anhydride was used instead of the starting stearic acid in Example 1-1 and reacted at 200° C.

Comparative Example 1-6

This Example was conducted in the same way as in Example 1-9, except for the kind of the catalyst, the amount of the catalyst and the amount of triphenylphosphine were changed to those shown in Table 3, the reactor was a 20 mL recovery flask that was subjected to the atmosphere substitution with nitrogen three times and connected to a vacuum pump, and the reaction was conducted under 33 kPa (absolute pressure).

Results of Examples 1-9 and Comparative Example 1-6 are collectively shown in Table 3.

TABLE 3

| | | Example 1-9 | Comparative example 1-6 |
|---|---|---|---|
| Catalyst | Kind | $NiCl_2(PPh_3)_2$ | $NiCl_2(PPh_3)_2$ |
| | Amount (%)*[1] | 1 | 1 |

TABLE 3-continued

|  |  | Example 1-9 | Comparative example 1-6 |
|---|---|---|---|
| Iodide | Kind | KI | KI |
|  | Amount (%)*1 | 10 | 10 |
| Amount of ligand PPh3 (%)*1*2 |  | 2 | 2 |
| Reaction temperature (° C.) |  | 200 | 200 |
| Pressure (kPa, absolute pressure) |  | 608 (when introduced) | 33 |
| CO concentration in gas phase (mmol/L) |  | 246 | 0~4.2 |
| Yield of olefin (%)*3 |  | 100 | 74 |
| contents of terminal olefin and internal olefin (%) | Terminal olefin | 9 | 42 |
|  | Internal olefin | 91 | 58 |

*1 A percentage by mole to a fatty acid anhydride
*2 Excluding a ligand originally coordinated to a catalyst
*3 amount to the mole number of a fatty acid anhydride Example 2-1

In a 30 mL stain-less auto clave containing a stirring bar, 284.5 mg (1.0 mmol) of stearic acid, 3.1 mg (0.01 mmol) of $NiI_2$, and 10.4 mg (0.04 mmol) of triphenylphosphine ($PPh_3$) were placed. The inner atmosphere was replaced with carbon monoxide three times by introducing carbon monoxide under 3000 kPa (absolute pressure) at a room temperature (25° C.) and reducing the pressure to the normal pressure. Then, carbon monoxide was introduced under 608 kPa (absolute pressure) at a room temperature. The reaction system was sealed, started with being stirred and heated, the stirring being continued at 250° C. for 3 hours. After the end of heating, the reaction mixture was allowed to cool to a room temperature (25° C.). Low-boiling matters were distilled off under reduced pressure. The mixture was analyzed by $^1$H-NMR spectroscopy to quantify products in the same way as in Example 1-1.

A yield of olefins was 21% (terminal olefin:internal olefins (molar ratio)=42:58) of the starting stearic acid.

Comparative Example 2-1

This Example was conducted in the same way as in Example 2-1, except that the reactor was a 20 mL recovery flask that was subjected to the atmosphere substitution with nitrogen three times and connected to a vacuum pump, and the reaction was conducted under 33 kPa (absolute pressure).

Results of Examples 2-1 and Comparative Example 2-1 are collectively shown in Table 4.

TABLE 4

|  |  | Example 2-1 | Comparative example 2-1 |
|---|---|---|---|
| Catalyst | Kind | $NiI_2$ | $NiI_2$ |
|  | Amount (%)*1 | 1 | 1 |
| Amount of ligand PPh3 (%)*1 |  | 4 | 4 |
| Reaction temperature (° C.) |  | 250 | 250 |
| Pressure (kPa Absolute pressure) |  | 608 (when introduced) | 33 |
| CO concentration in gas phase (mmol/L) |  | 246 | 0~3.8 |
| Yield of olefin (%) |  | 21 | 0 |
| ratio of terminal olefin and internal olefin (%) | Terminal olefin | 42 | — |
|  | Internal olefin | 58 | — |

*1 A percentage by mole to a fatty acid

Example 3-1

This Example was conducted in the same way as in Example 1-1, except that potassium iodide was not added.

Comparative Example 3-1

This Example was conducted in the same way as in Example 3-1, except that the reactor was a 20 mL recovery flask that was subjected to the atmosphere substitution with nitrogen three times and connected to a vacuum pump, and the reaction was conducted under 33 kPa(absolute pressure).

Results of Examples 3-1 and Comparative Example 3-1 are collectively shown in Table 5.

TABLE 5

|  |  | Example 3-1 | Comparative example 3-1 |
|---|---|---|---|
| Catalyst | Kind | $NiCl_2(PPh_3)_2$ | $NiCl_2(PPh_3)_2$ |
|  | Amount (%)*1 | 1 | 1 |
| Iodine | Kind | — | — |
|  | Amount (%)*1 | — | — |
| Ligand | Kind | $PPh_3$ | $PPh_3$ |
|  | Amount (%)*1*2 | 2 | 2 |
| Reaction temperature (° C.) |  | 250 | 250 |
| Pressure (kPa, absolute pressure) |  | 608 (when introduced) | 33 |
| CO concentration in gas phase (mmol/L) |  | 246 | 0~3.8 |
| Yield of olefin (%) |  | 14 | 1 |
| ratio of terminal olefin and internal olefin (%) | Terminal olefin | 75 | <1 |
|  | Internal olefin | 25 | >99 |

*1 A percentage by mole to a fatty acid
*2 Excluding a ligand originally coordinated to a catalyst Example 3-2

This Example was conducted in the same way as in Example 1-9, except that potassium iodide was not added.

Comparative Example 3-2

This Example was conducted in the same way as in Example 3-2, except that the kind of the catalyst and the amount of triphenylphosphine were changed to those shown in Table 6, the reactor was a 20 mL recovery flask that was subjected to the atmosphere substitution with nitrogen three times and connected to a vacuum pump, and the reaction was conducted under 33 kPa (absolute pressure).

Results of Examples 3-2 and Comparative Example 3-2 are collectively shown in Table 6.

TABLE 6

|  |  | Example 3-2 | Comparative example 3-2 |
|---|---|---|---|
| Catalyst | Kind | $NiCl_2(PPh_3)_2$ | $NiCl_2$ |
|  | Amount (%)*1 | 1 | 1 |
| Iodide | Kind | — | — |
|  | Amount (%)*1 | — | — |
| Amount of ligand PPh3 (%)*1*2 |  | 2 | 4 |
| Reaction temperature (° C.) |  | 200 | 200 |
| Pressure (kPa, absolute pressure) |  | 608 (when introduced) | 33 |
| CO concentration in gas phase(mmol/L) |  | 246 | 0~4.2 |
| Yield of olefin (%)*3 |  | 10 | 0 |

TABLE 6-continued

|  |  | Example 3-2 | Comparative example 3-2 |
|---|---|---|---|
| Contents of terminal olefin and internal olefin (%) | Terminal olefin | >99 | — |
|  | Internal olefin | <1 | — |

*[1] A percentage by mole to a fatty acid anhydride
*[2] Excluding a ligand originally coordinated to a catalyst
*[3] amount to the mole number of a fatty acid anhydride Materials used in Examples and Comparative Examples are as follows:

stearic acid: manufactured by Nacalai Tesque, Inc., catalog #32202-25 stearic anhydride: manufactured by Tokyo Chemical Industry Co., Ltd., catalog #S0083

$NiCl_2$ ($PPh_3$)$_2$: manufactured by Tokyo Chemical Industry Co., Ltd., catalog #B1571

[RhCl(CO)$_2$]$_2$: prepared from $RhCl_3 \cdot nH_2O$ (Tanaka Kikinzoku Hanbai K.K.)

IrCl(CO)$_3$: manufactured by ACROS ORGANICS, catalog #36355-1000

$PdCl_2$ ($PPh_3$)$_2$: prepared from $PdCl_2$ (manufactured by Wako Pure Chemical Industries, Ltd., catalog #162-00053)

CuCl: manufactured by Nacalai Tesque, Inc., catalog #09508-42

$NiI_2$: manufactured by Sigma-Aldrich Co. LLC., catalog #400777-5G $NiCl_2$: manufactured by Ishidu Seiyaku K.K., catalog #043-2761 triphenylphosphine: manufactured by Nacalai Tesque, Inc., catalog #35312-82 potassium iodide: manufactured by Wako Pure Chemical Industries, Ltd., catalog #162-19642

The invention claimed is:

1. A method for producing an olefin, comprising conducting decarbonylation of a carboxylic acid having a β-hydrogen atom or a derivative thereof in the presence of a catalyst comprising at least one metal element selected from the group consisting of a Group 9 metal, a Group 10 metal and a Group 11 metal under conditions with a concentration of carbon monoxide of not less than 41 mmol/L in the gas phase during the reaction.

2. The method for producing an olefin according to claim 1, wherein said decarbonylation is conducted in the presence of an iodide and said catalyst.

3. The method for producing an olefin according to claim 2, wherein the iodide is an iodide of an element selected from the group consisting of elements of Groups 1 to 8 and 12 to 14 or a quaternary ammonium compound represented by the formula (1):

$$[R-(Y)_n]_4N^+I^-  \quad (1)$$

wherein,

R represents a hydrocarbon group having 1 to 22 carbon atoms;

Y represents a group —Z—(CH$_2$)$_m$—,

Z represents an ether group, an amino group, an amide group or an ester group, m represents a number of from 1 to 6, and n represents 0 or 1; and plural R's, plural Y's, and plural n's each are the same as or different from one another, and a cyclic group may be formed between [R—(Y)$_n$]'s.

4. The method for producing an olefin according to claim 1, wherein said catalyst comprises an iodide of said at least one metal element selected from the group consisting of a Group 9 metal, a Group 10 metal, and a Group 11 metal.

5. The method for producing an olefin according to claim 1, wherein the carboxylic acid having a β-hydrogen atom or a derivative thereof is a carboxylic acid having a β-hydrogen atom or an anhydride of a carboxylic acid having a β-hydrogen atom.

6. The method for producing an olefin according to claim 1, wherein the metal element is at least one metal element selected from the group consisting of Co, Rh, Ir, Ni, Pd, Pt, Cu, Ag and Au.

7. The method for producing an olefin according to claim 1, wherein the metal element is at least one metal element selected from the group consisting of Co, Rh, Ir, Ni, Pd, Pt and Cu.

8. The method for producing an olefin according to claim 1, wherein the metal element is at least one metal element selected from the group consisting of Co, Rh, Ir, Ni, Pd and Pt.

9. The method for producing an olefin according to claim 1, wherein the metal element is Ni.

* * * * *